(12) United States Patent
White et al.

(10) Patent No.: US 7,516,924 B2
(45) Date of Patent: Apr. 14, 2009

(54) ARTICULATED BOOM FOR POSITIONING VIDEO AND MEDICAL EQUIPMENT IN HOSPITAL OPERATING ROOMS

(75) Inventors: Paul White, Lake Oswego, OR (US); Larry Vollum, Portland, OR (US)

(73) Assignee: CompView Corporation, Beaverton, OR (US)

( * ) Notice: Subject to any disclaimer, the term of this patent is extended or adjusted under 35 U.S.C. 154(b) by 366 days.

(21) Appl. No.: 11/093,075

(22) Filed: Mar. 28, 2005

(65) Prior Publication Data

US 2006/0226308 A1    Oct. 12, 2006

(51) Int. Cl.
*A47F 5/00* (2006.01)
*A47F 7/00* (2006.01)

(52) U.S. Cl. ............... 248/124.1; 248/123.11; 248/176.1; 248/276.1; 248/917; 248/919; 248/921; 359/384

(58) Field of Classification Search .............. 248/124.1, 248/123.11, 123.2, 917–923; 359/384, 368, 359/363, 392
See application file for complete search history.

(56) References Cited

U.S. PATENT DOCUMENTS

| | | | |
|---|---|---|---|
| 4,548,373 A | | 10/1985 | Komura |
| 5,061,018 A | * | 10/1991 | Pederson et al. ............ 312/209 |
| 5,748,366 A | * | 5/1998 | Yasunaga et al. ............ 359/368 |
| 5,944,291 A | * | 8/1999 | Kato et al. ............... 248/188.2 |
| 6,012,821 A | | 1/2000 | Yeaney et al. |
| 6,202,360 B1 | | 3/2001 | Rattner et al. |
| 6,328,458 B1 | | 12/2001 | Bell et al. |
| 6,639,789 B2 | | 10/2003 | Beger |
| 6,661,571 B1 | * | 12/2003 | Shioda et al. ............... 359/372 |
| 6,715,673 B2 | * | 4/2004 | Fulcher et al. .............. 235/381 |
| 6,732,988 B2 | | 5/2004 | Ihalainen et al. |
| 6,793,625 B2 | | 9/2004 | Cavallaro et al. |
| 6,817,585 B2 | | 11/2004 | Wagner et al. |
| 6,840,486 B2 | | 1/2005 | Kuhn |
| 6,857,609 B2 | | 2/2005 | Stoianovici et al. |
| 6,896,233 B2 | | 5/2005 | Kuhn |
| 7,110,173 B2 | * | 9/2006 | Haisch ........................ 359/384 |
| 7,246,780 B2 | * | 7/2007 | Oddsen, Jr. ............... 248/282.1 |
| 2004/0188578 A1 | * | 9/2004 | Turner ................... 248/281.11 |

(Continued)

FOREIGN PATENT DOCUMENTS

DE    9218373    12/1992

(Continued)

*Primary Examiner*—Amy J. Sterling
(74) *Attorney, Agent, or Firm*—Beyer Law Group LLP

(57) ABSTRACT

The present invention is directed to a stationary medical boom that can be easily installed on the floor of an existing operating room and that has one or more articulated arms used to position audio, video and medical equipment over an operating table in an operating room. The boom includes a stationary base configured to be attached to the floor of the operating room. One or more articulated boom arms are supported by the stationary base and extend out over the operating table. Articulated appendage arms, extending from the boom arms, are configured to support the audio, video and other medical equipment used in the operating room in the vicinity of the operating table. Both the articulated boom arm and the articulated appendage arm can be moved in either the X and/or Y directions. Consequently, the equipment supported by the appendage arm can be moved in virtually any position around the operating table.

58 Claims, 12 Drawing Sheets

U.S. PATENT DOCUMENTS

| | | | |
|---|---|---|---|
| 2004/0193453 A1* | 9/2004 | Butterfield et al. | 705/2 |
| 2004/0195471 A1* | 10/2004 | Sachen, Jr. | 248/127 |
| 2006/0065795 A1* | 3/2006 | Blackburn | 248/122.1 |

FOREIGN PATENT DOCUMENTS

| | | |
|---|---|---|
| DE | 9218373.5 | 12/1992 |
| DE | 19807241 | 2/1998 |
| DE | 19807242 | 2/1998 |
| DE | 19807243 | 2/1998 |
| DE | 19807241 | 8/1999 |
| DE | 19807242 | 8/1999 |
| DE | 19807243 | 8/1999 |
| EP | 0876799 | 11/1998 |
| WO | WO 99/23989 | 5/1999 |
| WO | WO 02/30348 | 4/2002 |

* cited by examiner

ARTICULATED BOOM FOR POSITIONING VIDEO AND MEDICAL EQUIPMENT IN HOSPITAL OPERATING ROOMS

FIELD OF THE INVENTION

The present invention relates generally providing medical personal access to audio, visual and medical equipment in a hospital operating room, and more particularly, to a medical boom that provides a universal connection point for needed services in the operating room, including audio and video inputs and outputs, power, fluid delivery and recovery, and gases. The medical boom includes a stationary base with and one or more articulated arms supported by the base. The articulated arms provide 360 degree positioning of audio, visual and medical equipment around the operating field.

BACKGROUND

State of the art hospital operating rooms now contain a wide variety of audio, visual and technology tools, such as video cameras, video recorders, microphones and voice recorders, video guided ultrasound imaging systems, lasers, cytoscanners, etc. With delicate surgery for example, a 3D video camera may be placed in or above the surgical area of the patient. The image from the camera is then transmitted to a large display, such as a flat panel, so that the operating doctor and medical staff can see an enlarged visual of the surgical area. The enlarged image makes it easier for the doctor to perform the surgery compared to relying on the naked eye.

To accommodate all the audio, visual and medical equipment, many operating rooms have been built or retrofitted to include one or more booms suspended from the ceiling. The audio and visual equipment is then hung from the booms over the operating table. There are a number of problems, however, associated with using booms suspended from the ceiling. Most hospitals were built before many of the medical procedures commonly used today that require the use of the above described audio and visual equipment. As a result, operating rooms were not built with the requisite ceiling booms to suspend the equipment. Rather, the operating rooms have been retrofitted to install the ceiling booms. The retrofit process, however, is very complicated and expensive. Often an architect is required to draw up the plans and to provide structural engineering services. The plans are then submitted to the local building department for review. After the plans are approved, the operating room is shut down, and construction begins. The retrofit typically involves structurally reinforcing the ceiling prior to installing the booms and equipment. In addition, other trades, such as electricians, are need to upgrade the electrical power and lighting systems. A retrofit project will therefore take at least several months and cost well into the six figure dollar amount. Since the operating room can not be used during the construction, the retrofit process also results in a significant loss of revenue for the hospital. With newer hospitals, the cost and expense of designing and implementing the boom system from the ceiling during construction is also considerable.

A stationary medical boom that can be readily installed on the floor of an existing operating room, resulting in less down time, and that has one or more articulated arms used to position video and medical equipment 360 degrees around the operating table in an operating room and is capable of providing a universal connection point for needed services in the operating room, is therefore needed.

SUMMARY OF THE INVENTION

The present invention is directed to a stationary medical boom that can be easily installed on the floor of an existing operating room and that has one or more boom arms used to position audio, video and medical equipment over an operating table in an operating room. The medical boom includes a stationary base configured to be attached to the floor of the operating room. One or more boom arms are supported by the stationary base and extend out over the operating table. Articulated appendage arms, extending from the boom arms, are configured to support the audio, video and other medical equipment used in the operating room in the vicinity of the operating table. Both the articulated boom arm and the articulated appendage arm can be moved in either the X and/or Y directions. Consequently, the equipment supported by the appendage arm can be moved in virtually any position around the operating table. The stationary base acts as a universal connection point and houses electronic equipment for providing medical, video and data processing services for the operating field.

The medical boom thus provides a number of advantages, including improved viewing angles for a more comfortable setting for the surgeon and medical staff. Since the stationary base is mounted onto the floor in an operating room, the aforementioned issues of using ceiling booms to suspend equipment is avoided. The medical boom of the present invention can also be installed in an operating room in a few days or less, resulting in less "down time" of the operating room. The stationary base can be used to house a host of electronic and medical equipment. It thus provides a centralized control station that can be readily accessed by the surgeon and medical staff. The medical boom can also be configured to deliver services, such as power and control electrical signals, gases, fluids, and fluid recovery from the patient.

These and other features and advantages of the present invention will be presented in more detail in the following specification of the invention and the accompanying figures, which illustrate, by way of example, the principles of the invention.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE INVENTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known operations have not been described in detail so not to unnecessarily obscure the present invention.

Figure 1:
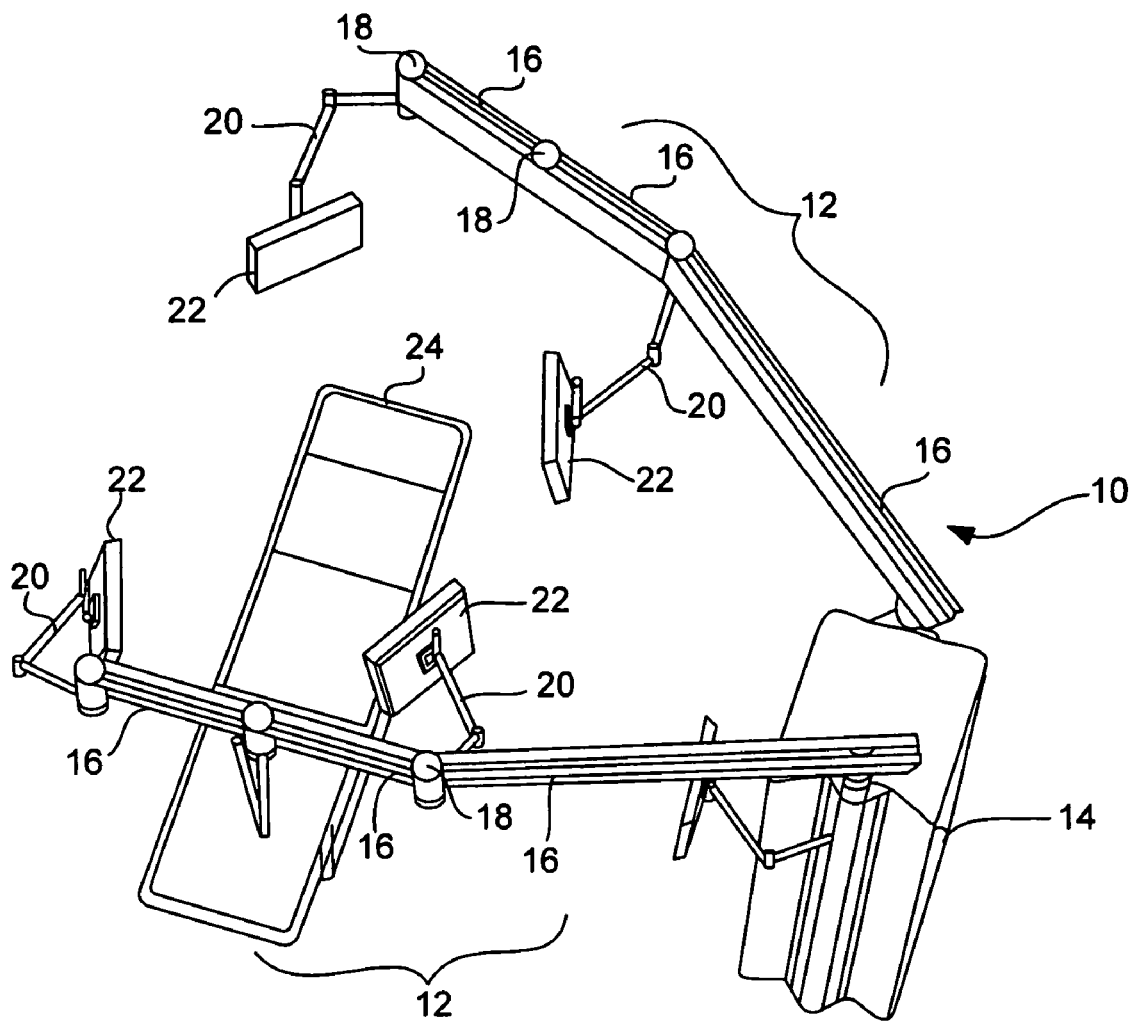
FIG. 1 illustrates a perspective view of the medical boom in an operating room according to the present invention.

Referring to FIG. 1, a perspective view of the medical boom in an operating room according to the present invention is shown. The medical boom 10 includes one or more articulated boom arms 12 mounted onto a stationary base 14. Each articulated boom arm 12 is made from a number of arm segments 16 held together by joints 18. One or more articulated appendage arms 20 are also attached to each articulated boom arm 12. The appendage arms 20 are used to suspend camera, audio, visual and/or medical equipment from the articulated boom arm 12. For example, as illustrated in the figure, four display monitors 22 are suspended from the appendage arms 20 over an operating table 24 in a hospital operating room. Both the articulated boom arms 12 and the articulated appendage arms 20 can be moved in the X and Y directions. As a result, the display monitors (or any other audio, video, or medical equipment) attached to the articulated boom arms 12 and the appendage arms 20 can be readily moved to any desired horizontal and vertical position by the surgeon or support medical staff. The articulated boom arms 12 and appendage arms 20 thus provide equipment and display positioning 360 degrees around the operating field.

The stationary base 14 not only supports the articulated boom arms 12, but also can be used to house a host of medical and electronic equipment, such as computers, video processors, communication equipment, a programmable control system which provides the centralized controls, and switching of equipment. The articulated boom arms 12 and the articulated appendage arms 20 can also be configured to carry both wiring and tubing between the electronic and medical equipment housed in the stationary base 14 and the audio, visual, and medical equipment attached to the appendage arms 20. The tubing can be used for fluid and/or gas delivery to and recovery from the patient.

According to various embodiments of the invention, the length and number of the individual segments 16 of the articulated boom arms 12 may vary. In the embodiment shown in FIGS. 1 through 3 for example, the segment 16 of both articulated boom arms 12 closest the stationary base 14 are longer than the other segments 16 of each arm. In other embodiments, however, the length of each segment 16 can all be the same, or they can be of different lengths, with shorter segments 16 closer and longer segments 16 farther from the base 14, or vice versa. Further, the number of segments 16 per articulated boom arm 12 may be either more or less than three as illustrated in the figures. The arrangement shown in the figures should therefore not be construed as limiting the scope of the present invention.

Figure 2:
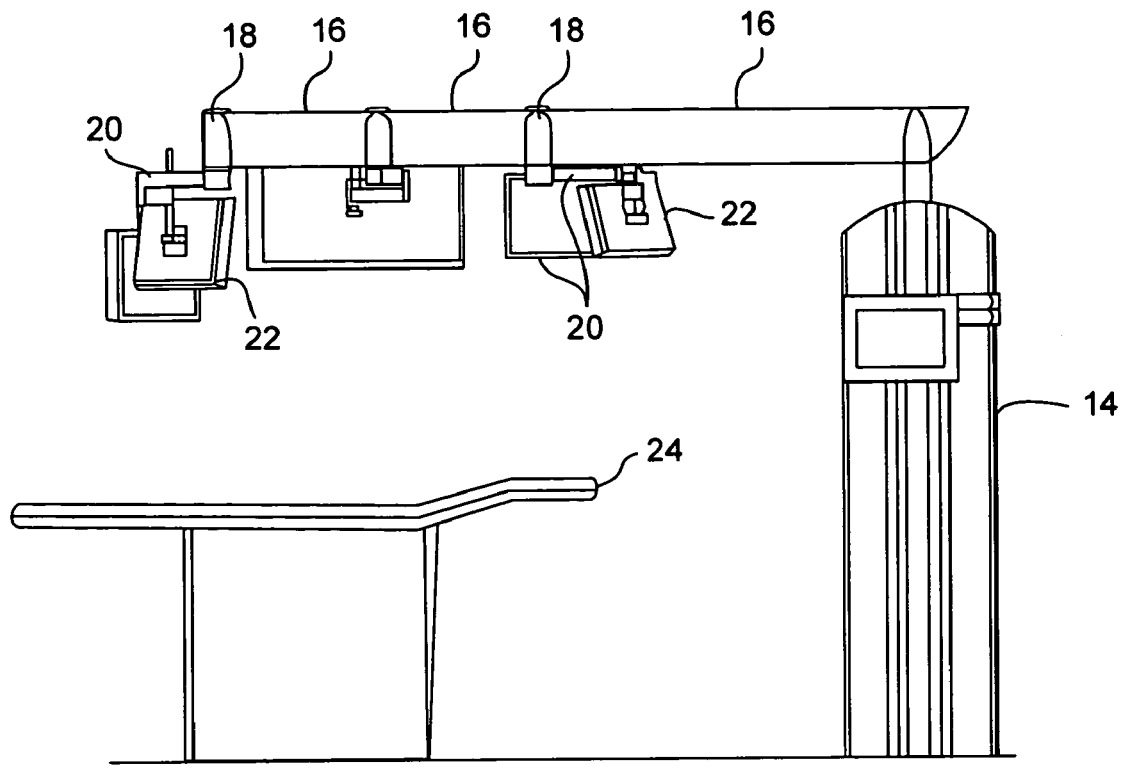
FIG. 2 illustrates a side view of the medical boom in an operating room according to the present invention.
Figure 3:
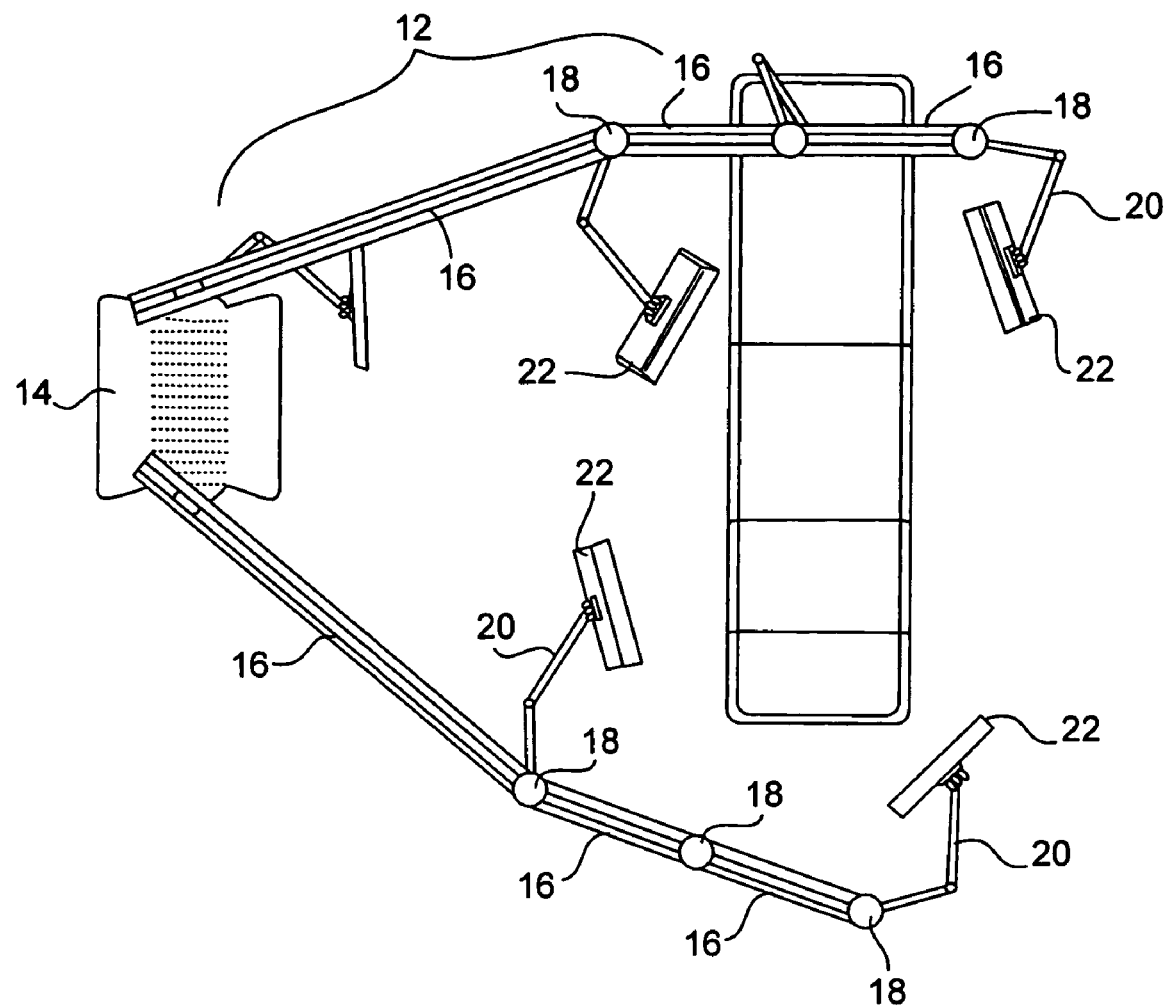
FIG. 3 illustrates a top-down view of the medical boom in an operating room according to the present invention.

Referring to FIGS. 2 and 3, side and top views of the medical boom 10 according to the present invention are shown respectively. In these views, the articulated boom arms 12 are shown extending from the stationary base 14 over the operating table. The display monitors 22, suspended from the articulated appendage arms 20, are thus within easy reach of the surgeon or other medical personal around the operating table. The ability of both the articulated boom arms 12 and the articulated appendage arms 20 to each move in the X, Y and Z directions allows the monitors 22 (or any other supported equipment) to be moved in six degrees of freedom and positioned in any desired position 360 degrees around the operating field surrounding the operating table.

Figure 4A:
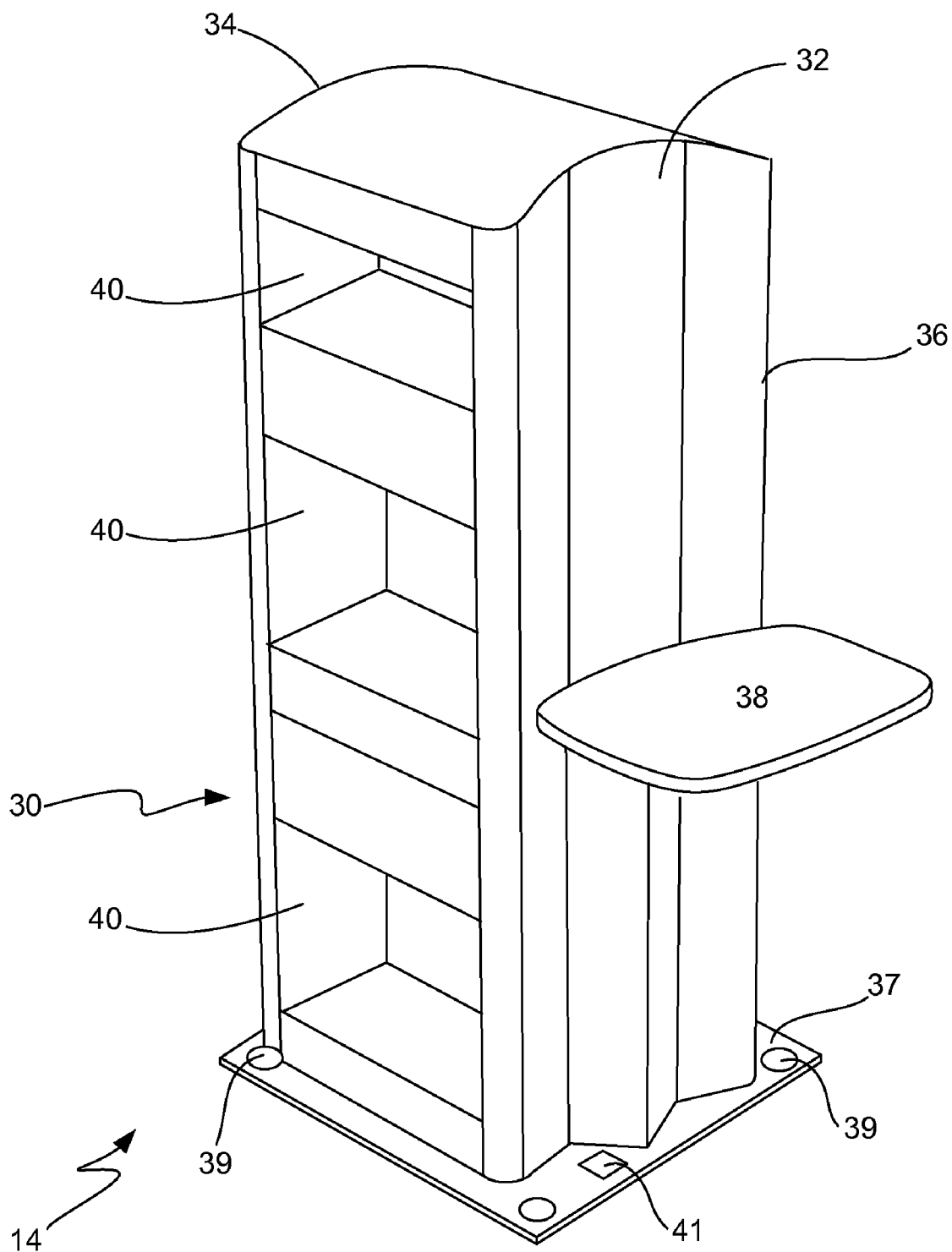
FIGS. 4A-4C illustrate various views of a stationary base of the medical boom according to the present invention.
Figure 4B:
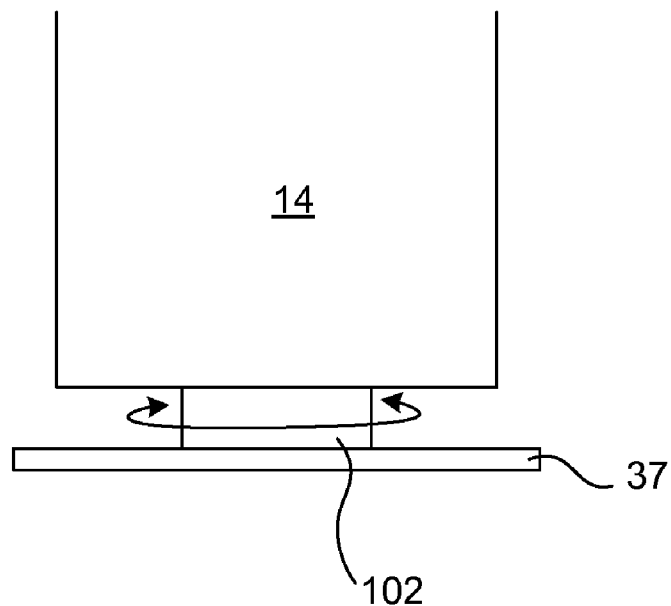
Figure 4C:
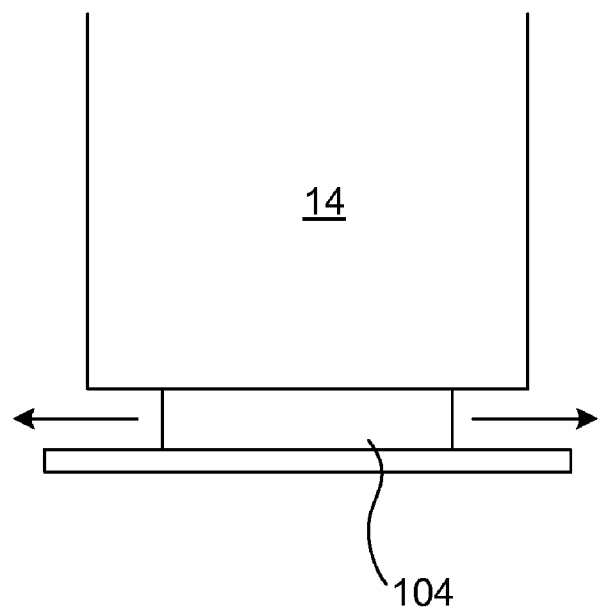

Referring to FIG. 4A, a front perspective view of the stationary base 14 of the medical boom according to the present invention is shown. (for the sake of simplicity, the articulated arms 12 are not shown in the figure) The stationary base 14 is a standing structure having a front panel 30, two side panels 32 and 34, a rear panel 36, and an optional shelf 38 (or multiple shelves) extending from one or both of the side panels 32 or 34. The stationary base 14 is supported on a base plate 37. The base plate is configured to be mounted to the floor using a fastening mechanism 39, such as a number of bolts used to secure the base plate 37 to the floor. The front panel 30 includes a number of recess regions 40 for housing a host of medical and electronic components (not illustrated in the figure), such as computers, video processors, communication equipment. Typically the medical and electronic components are inserted into the recess regions 40 so that their front panels are accessible. In this manner, the controls usually found on such components, such as knobs, push buttons and the like, are within easy reach by the surgeon or medical staff. The shelf 38 can be used for a number of purposes, such as for shelving medical equipments like scalpels and syringes or a computer keyboard and mouse for a computer housed in the stationary base 14. In the embodiment described above, the base is stationary when bolted to the floor. In other embodiments, however, the stationary base 14 can be designed to rotate using a rotating member 102 between the stationary base 14 and the base plate 37 as illustrated in FIG. 4B or slide back and forth on the base plate 37 by providing a sliding member 104 between the stationary base 14 and the base plate 37 as illustrated in FIG. 4C. A locking mechanism 41, such as a bolt, screw, or pin, is used to lock the stationary base 14 in place after it has been moved to a desired position. Thus the term "stationary" does not necessarily mean that the stationary base 14 is permanently or immovably mounted to the floor, but can be affixed to the floor but movable.

Figure 5:
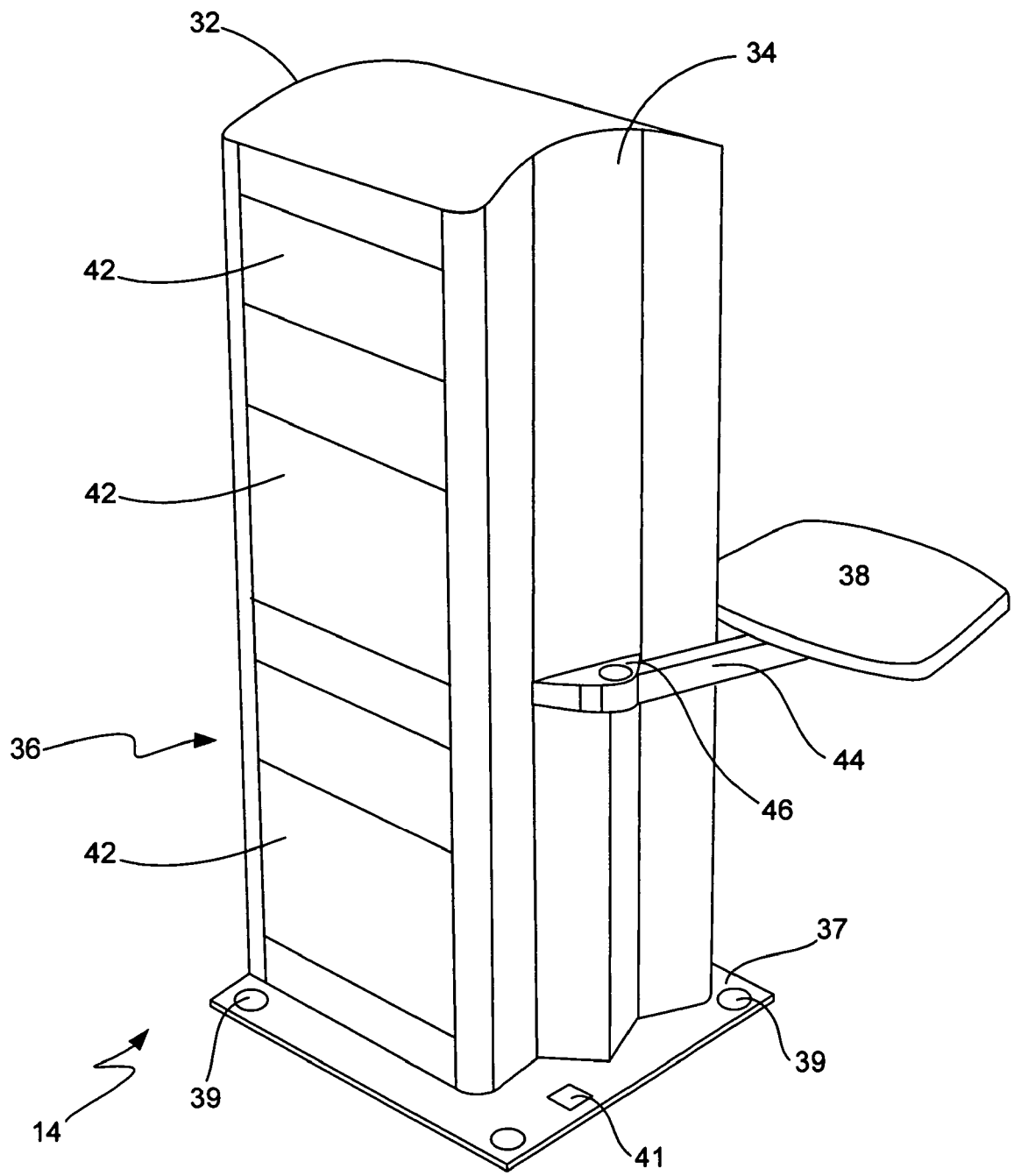
FIG. 5 illustrates a rear perspective view of the stationary base of the medical boom according to the present invention.

Referring to FIG. 5, a rear perspective view of the stationary base 14 of the medical boom 10 according to the present invention is shown. In this view, the rear panel 36 is visible and includes a plurality of recesses 42 that provide access to the back of the medical and electrical components that may be housed in the stationary base 14. The recesses 42 are convenient because they allow the medical staff and other technical personal to access cables, power cords, and the like attached to the components housed in the stationary base 14. The rear perspective view also illustrates an arm 44, attached to side panel 34, by a joint 46, used to support the shelf 38. The joint 46 enables the shelf 38 to be rotated or moved into a desired position adjacent the stationary base 14.

The stationary base 14 thus provides a central location where electronics and medical equipment can be conveniently stored. The electronics for the routing, switching and display of audio, video and control signals can be housed in the stationary base 14. The stationary base 14 can also provide access ports for digital image capture and print equipment, network equipment, Internet access, etc. In addition, the stationary base 14 can also provide a universal connection for providing services to the operating field, such as gases, control signals, power, and audio and visual input signals.

Figure 6:
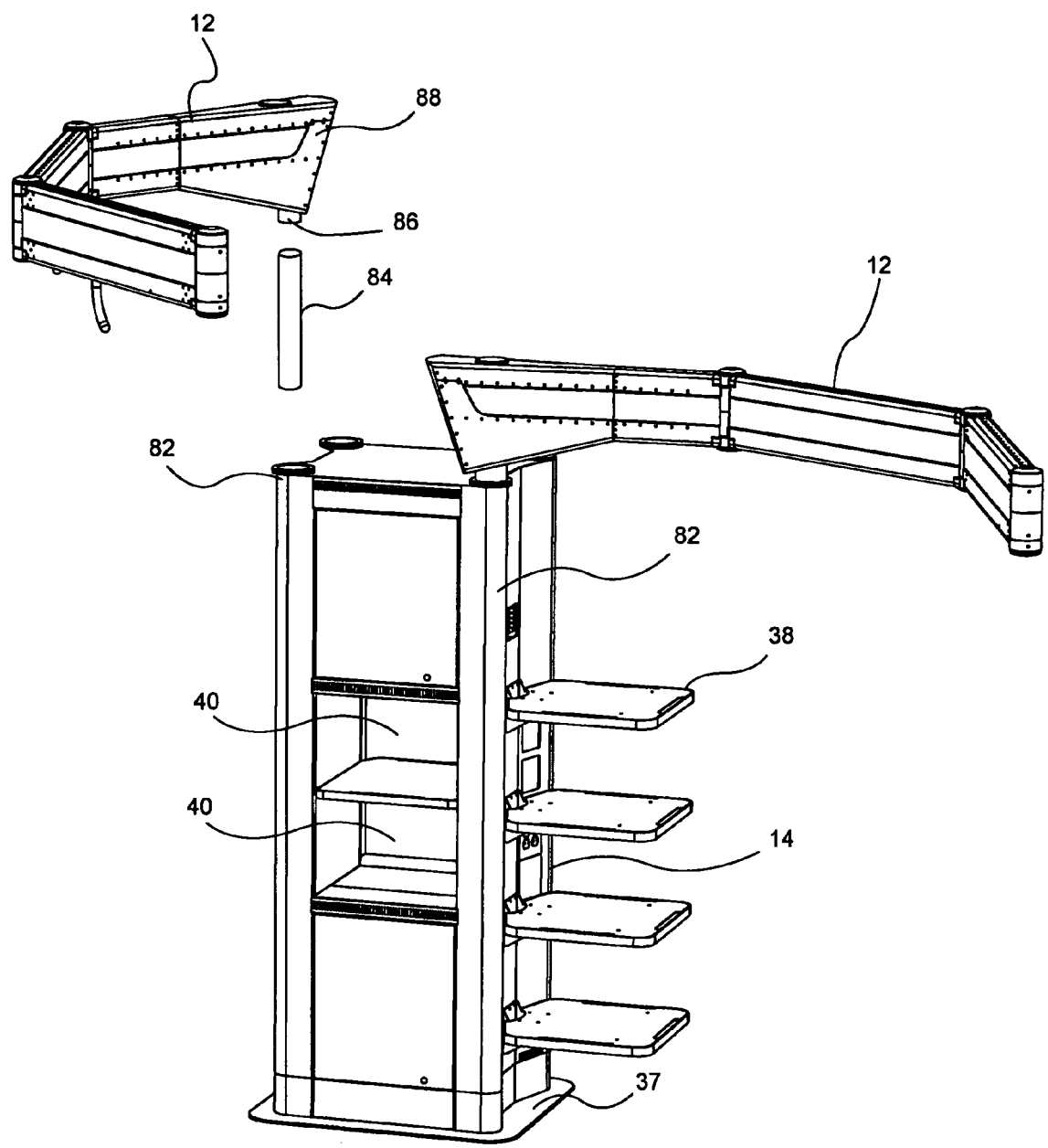
FIG. 6 illustrates a perspectives view of an articulated arm attached to the base of the medical boom of the present invention.

Referring to FIG. 6, a perspective view illustrating how an articulated arm 12 is attached to the stationary base 14 is shown. Cylindrical shaped receptacles 82 are provided at the upper corners of the stationary base 14. The receptacles 82 are configured to receive a pin 84 that is inserted into the receptacle 82. The articulated boom arm 12 also includes a cylindrical shaped receptacle 86 configured to slide over the top portion of the pin 84. The articulated boom arm 12 is thus designed to friction-rotate about the pin 84 so that position of the arm can be moved in the horizontal plane. In an alternative embodiment, a hinge 88, provided at the base of the articulated boom arm 12 above the cylindrical shaped receptacle 86, enables the articulated boom arm 12 to be positioned in the vertical direction.

Figure 7:
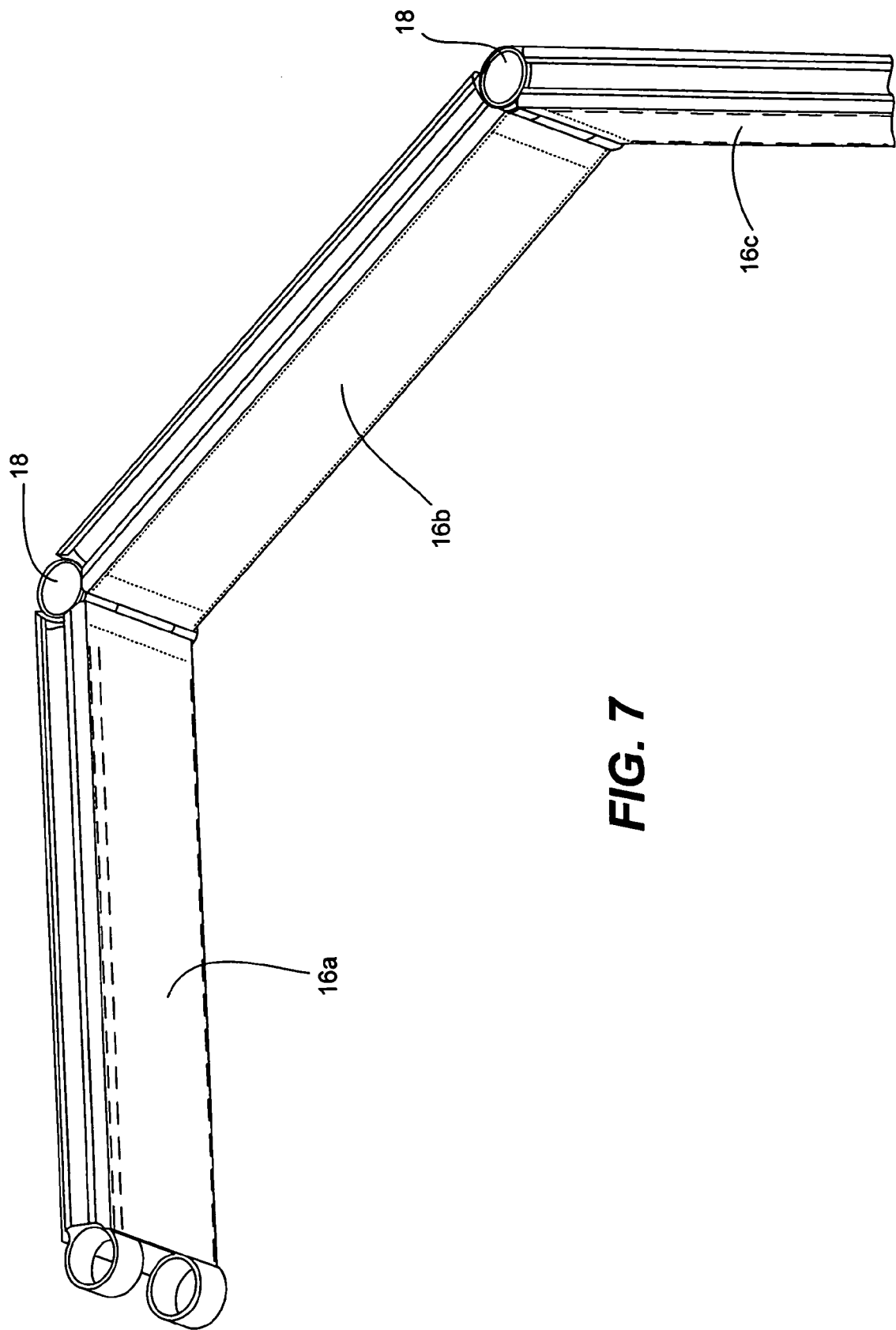
FIG. 7 illustrates the segments and joints of an articulated arm of the medical boom of the present invention.

Referring to FIG. 7, the segments 16 and joints 18 of an articulated boom arm 12 of is shown. In this Figure, three segments 16a, 16b and 16c are shown mechanically coupled by two rotating joints 18a and 18b respectively. The individual segments 16a, 16b and 16c can thus each be rotated about the joints 18a and 18b respectively.

Figure 8A:
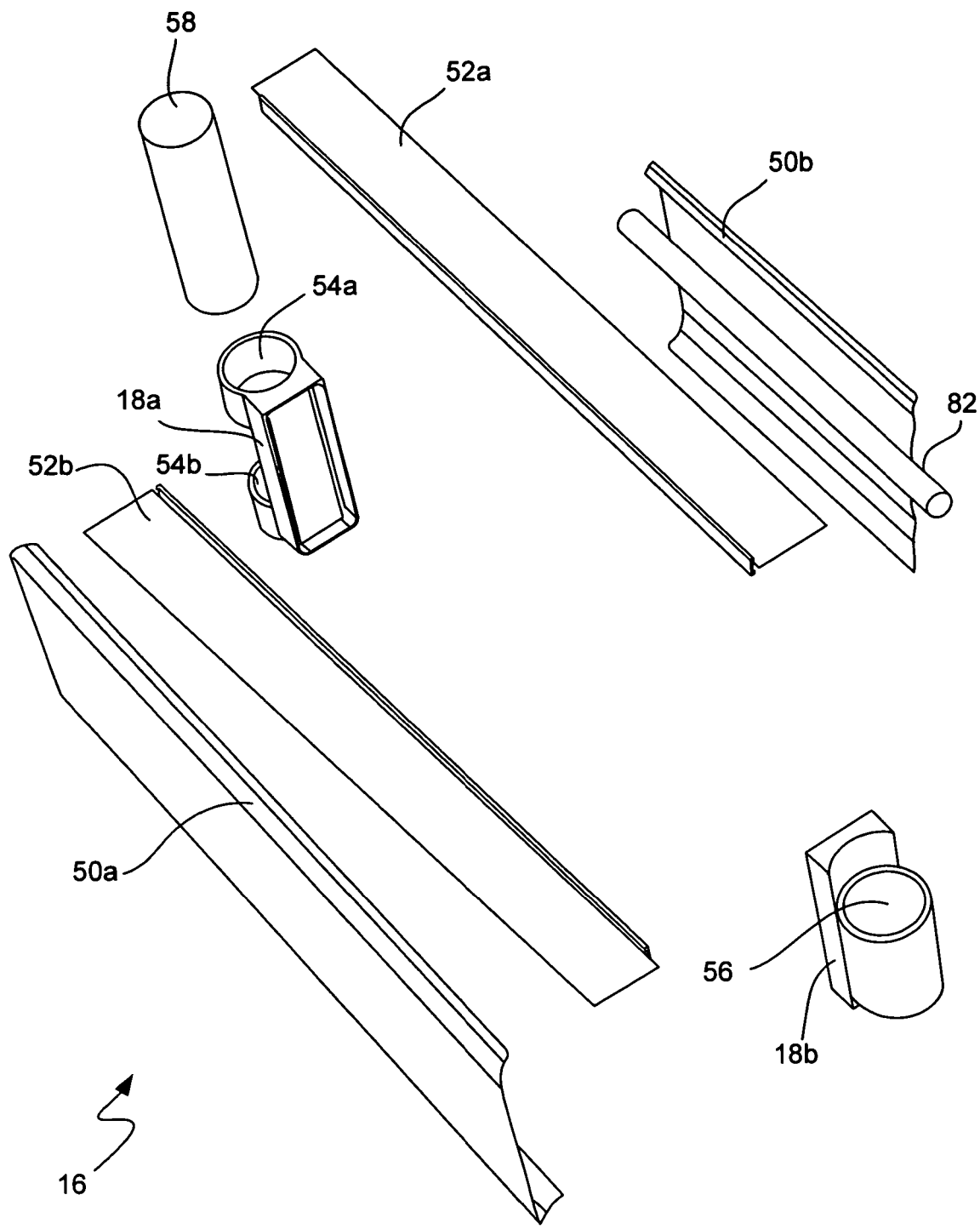
FIGS. 8A and 8B illustrate an exploded views of a joint used to connect two segments of the articulated arm of the medical boom according to two embodiments of the present invention.

Referring to FIG. 8A, an exploded view of the component parts of a segment 16 and a joint 18 according to one embodiment is shown. The component parts of the segment 16 include two side members 50a and 52b, a top member 52a, and a bottom member 52b. A conduit 82 may also be provided within the segment 16. The conduit 82 may be used for providing a passage way for tubing for gas delivery and recovery and electrical wires through the segment 16 (e.g., electrical signal wires, electrical power wires, gas hoses and fluid hoses). With such embodiments, the conduit would run from the stationary base 14, along the length of each segment 16 of articulated arm 12, and through the appendage arms 20 to the equipment mounted onto the appendage arm 20. The joints 18 would include recesses to allow the conduit to pass from one segment 16 to the next and between the articulated arm 12 and the appendage arm 20.

The four members 50a, 50b, 52a and 52b are affixed together to form a segment 16. According to various embodiments, the four members 50a, 50b, 52a and 52b can be made from a plastic, carbon fiber, metal or metal alloy, such as aluminum or steel. They can be affixed together in a number of various ways. With metal embodiments for example, the four members 50a, 50b, 52a and 52b can be stamped or machined individually and then affixed for example by welding, bolting or screwing, riveting the individual parts together. With plastic or carbon fiber embodiments, the four members 50a, 50b, 52a and 52b, can be formed together in a mold or the individual component parts can be affixed together using a glue or other compound for example. In an alternative embodiment, one or more of the component members 50a, 50b, 52a and 52b may be removable for servicing in the field and to provide access to any wires or tubes running through the segments 16 of the articulating boom arm 12.

It should be noted that the segments 16 need not be fabricated from a number of component parts affixed together. In other embodiments, the segments 16 can be fabricated from a single component part, such as molded plastic or carbon fiber, machined metal or cast metal for example.

The component parts of each joint 18 include two mating sleeves 18a and 18b. The first sleeve 18a includes an upper 54a and a lower 54b receptacle. The second sleeve 18b includes a middle receptacle 56. When adjacent segments 16 are assembled, the sleeves 18a and 18b are mated together by inserted the middle receptacle 56 between the upper 54a and lower 54b receptacles. A pin 58 is then inserted through the three receptacles 54a, 54b and 56, holding the two mating sleeves 18a and 18b together. In one embodiment, the pin 58 provides sufficient friction with the receptacles 54a, 54b and 56 such that the adjacent segments 16 will not move or drift unless purposely repositioned by the surgeon or other medical personal.

Figure 9:
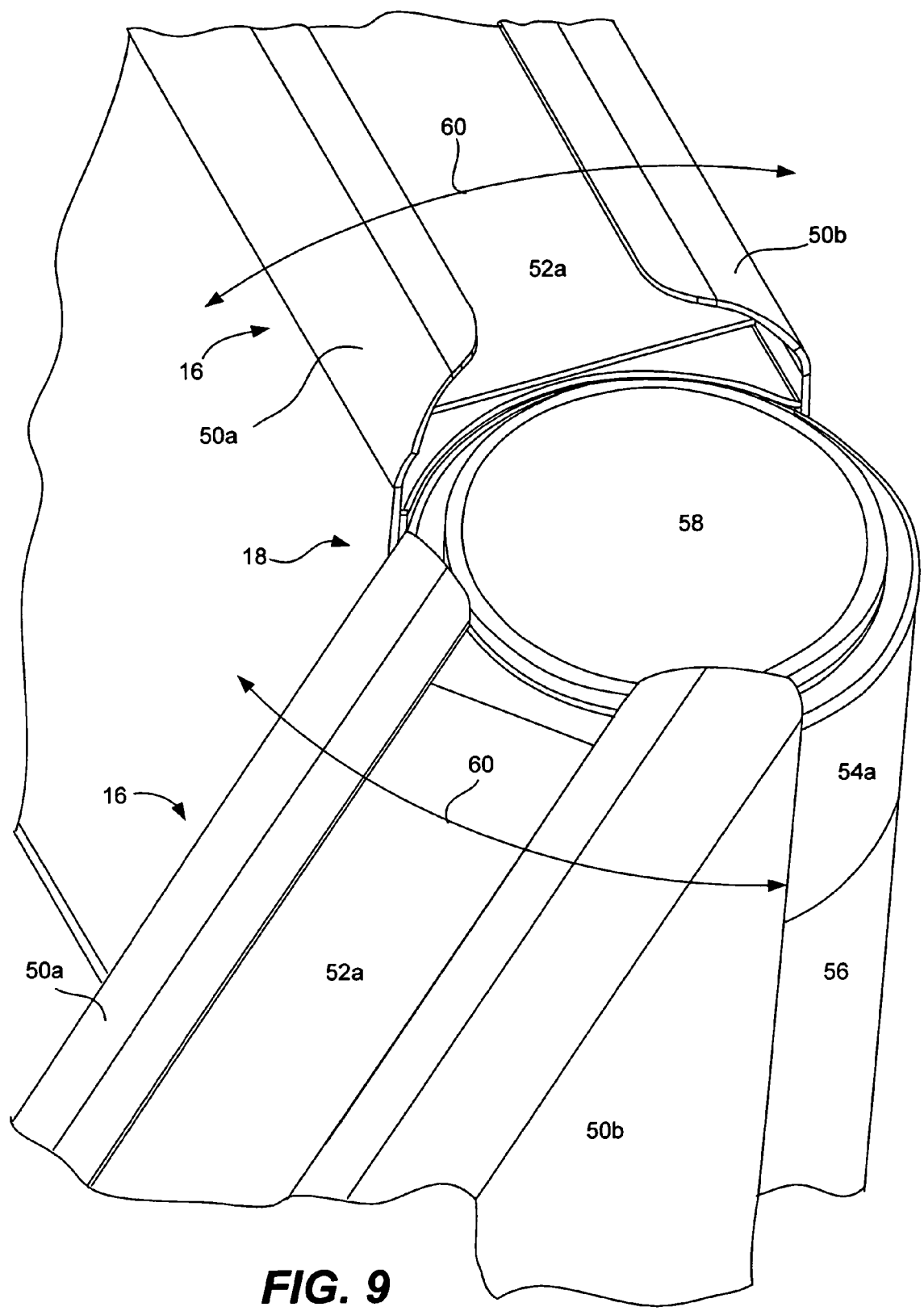
FIG. 9 illustrates a perspective view of the component parts of a segment and joint of the articulated arm of the medical boom of the present invention.

Referring to FIG. 9, a perspective view of an assembled joint 18 mating two segments 16 of an articulated arm boom 12 is shown. The figure shows the pin 58 inserted through the receptacles 54a, 56 (receptacle 54b is not visible) of joint 18 which holds two adjacent segments 16 together. The two segments 16 are each free to be rotated about the pin 58 of the joint 18 as indicated by the arrows 60.

Figure 8B:
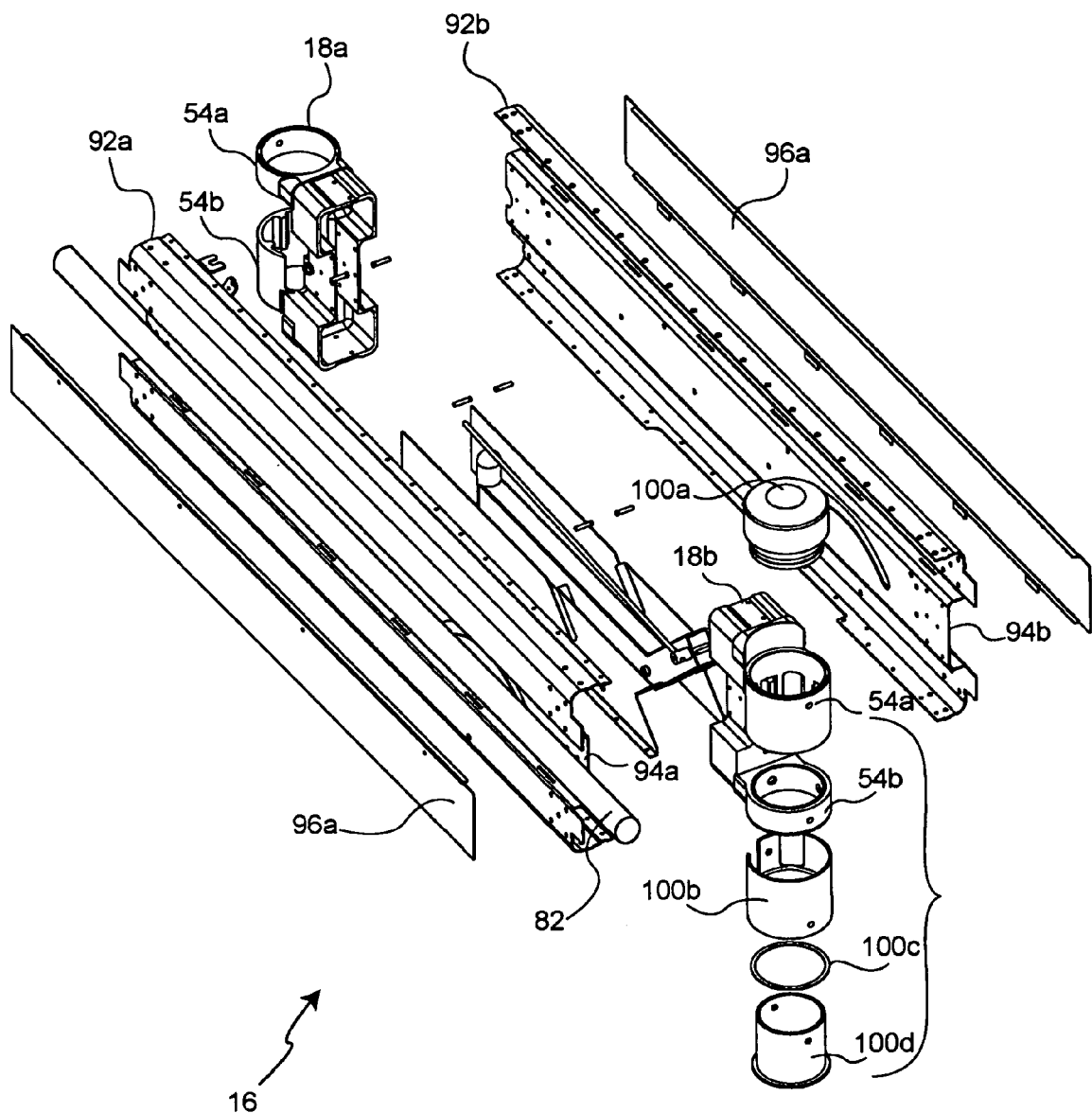

Referring to FIG. 8B, a segment 16 according to another embodiment is shown. In this embodiment, two side members 92a and 92b are provided. Each side member 92a and 92b includes elongated recesses 94a and 94b respectively running the length of each member. The recesses 94a and 94b are provided for accommodating a conduit 82 for carrying wires, tubes, and other passage ways for distributing electrical signal wires, electrical power wires, gas hoses and fluid hoses and the like. As previously noted, the conduit runs between segments 16 of articulated arm 12 and through the appendage arms 20 so that gas, fluid and electrical services can be provided between the base 14 and the operating field. Covers 96a and 96b are used to cover the recess regions 94a and 94b of side members 92a and 92b respectively. In one embodiment, the side covers 96a and 96b are removable so that the conduit and any other internal wires or tubes are accessible and can be services in the field. The segment 16 in this embodiment also includes a bottom element 98. Joints 18a and 18b are provided at each end of the segment 16. Each joint has a receptacle 54a and 54b. Rather than using a single pin 58 as illustrated in FIG. 8A, a multi-segment elements 100a-100d can be inserted into the receptacles 54a and 54b respectively. Specifically elements 100a and 100d are threaded and are configured to be screwed into the receptacles 54a and 54b respectively to hold two adjacent segments 16 and the components of the joint 18 together.

In various other embodiments, the elements 92a and 92b can be fabricated from metal, plastic, carbon fiber, etc. The elements of the segment 16 including the side members 92a and 92b, bottom element 98 and joints 18a and 18b are fastened together using any type of fastening element, including but not limited to bolts, screws, rivets, glue or other compounds, or the like.

Figure 10:
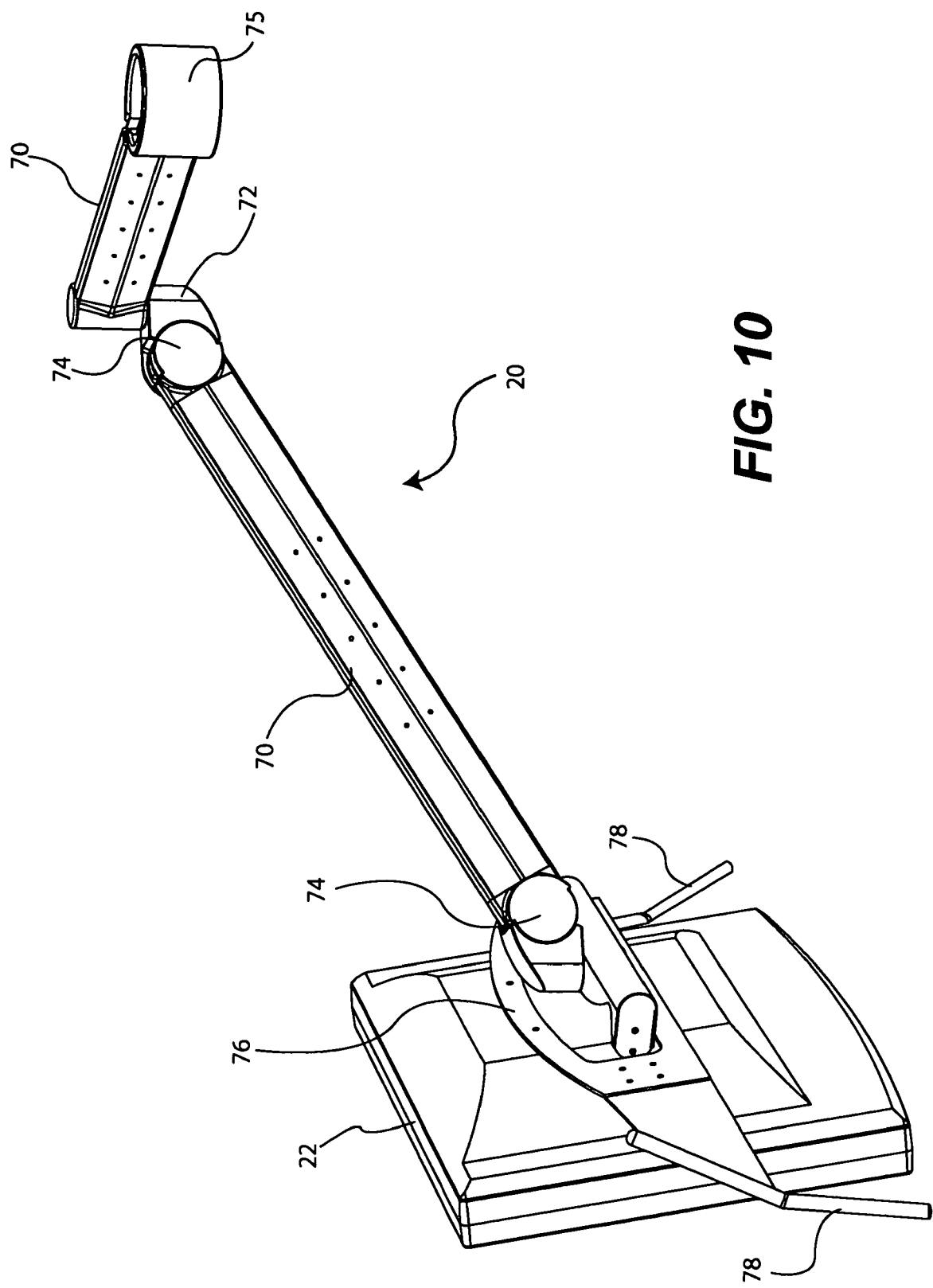
FIG. 10 shows a back perspective views of a display monitor mounted onto an appendage arm of the medical boom of the present invention.

Referring to FIG. 10, a rear view of a display monitor 22 mounted onto an articulated appendage arm 20 according to the present invention is shown. The articulated appendage arm 20 includes a number of segments 70. The segments 70 can be fabricated in the various ways described above with respect to the segments 16 as described in relation to FIG. 8A and/or FIG. 8B. The segments 70 are connected together using a combination of pin joints 72 and rotating joints 74. The pin joints 72 enable the monitor 22 to be moved from side to side in the horizontal plane whereas the rotating joints enable the monitor 22 to be moved up and down in the vertical plane. A rotating joint 75 connects the appendage arm 20 to a boom arm 12 (not shown). A mounting plate 76 is provided to mount the monitor 22 onto the articulated appendage arm 20.

Handles 78, attached to the mounting plate 76, are used to move and position the monitor 22.

In one embodiment, one or more of the monitors 22 may be a touch screen display that may be configured to control the medical and electrical components that may be housed in the stationary base 14. In this embodiment, the one or monitors are configured to generate a touch-screen input display. The display is coupled to the electronic and medical equipment housed in the stationary base 14 through electrical wires running through the conduit 82 of the articulated arm boom(s) 12 and articulated appendage arm(s) 20 between the one or more touch screen monitors 22 and the stationary base 14. The touch screen displays 22 thus provide a touch panel interface that enables the operating doctor and other medical personal in the operating field to control, switch, and route signals to the electronic and medical equipment housed in the stationary base 14.

While this invention has been described in terms of several preferred embodiments, there are alteration, permutations, and equivalents, which fall within the scope of this invention. For example, the stationary base does not necessarily have to be fastened to the floor of an operating room. It can also be attached to or affixed to the wall of an operating room. Further, while the present invention has been described as a medical boom for use in a hospital operating room, it does not necessarily have to be limited to this environment. Rather the boom of the present invention may be used in a dentist office, examination rooms, veterinary clinics, surgical suites, etc. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

We claim:

1. A medical boom, comprising:
   a stationary base configured to be installed into an operating room;
   a plurality of boom arms, each of the plurality of boom arms being supported by the stationary base and configured to extend over an operating table in the operating room and having at least an associated pair of boom arm segments that are coupled together by a boom arm joint; and
   a plurality of appendage arms, each appendage arm being mounted on an associated boom arm and having at least an associated pair of appendage arm segments that are coupled together by an appendage arm joint, each of the appendage arms being configured to support an associated display monitor that can be positioned in the horizontal and the vertical planes substantially surrounding the operating table, wherein a first appendage arm of the plurality of appendage arms is mounted on an attachment joint mounted on one of the boom arm segments associated with a first one of the boom arms, the attachment joint being situated between first and second ends of the first one of the boom arms.

2. The medical boom of claim 1, further comprising a base joint to mount at least one of the plurality of boom arms onto the stationary base, the base joint enabling the at least one of the plurality of boom arms to be moved in either the horizontal plane, the vertical plane, or both the horizontal and vertical planes.

3. The medical boom of claim 1, wherein the stationary base further comprises recess regions configured to house medical and/or electronic equipment.

4. The medical boom of claim 1, wherein the stationary base further comprises a base plate and a fastening element configured to secure the base plate to the floor of an operating room.

5. The medical boom of claim 4, wherein the base plate is configured to move relative to the fastening element so that the stationary base may be moved relative to the floor of the operating room.

6. The medical boom of claim 5, wherein the base plate further comprises a locking mechanism configured to lock the stationary base in place after it has been moved to a desired position.

7. The medical boom of claim 1, wherein the boom arm segments are rotationally coupled to the associated boom arm joints.

8. The medical boom of claim 1, wherein the boom arm segments are rotationally coupled to the associated boom arm joints in the horizontal plane.

9. The medical boom of claim 1, wherein the boom arm segments are rotationally coupled to the associated boom arm joints in the vertical plane.

10. The medical boom of claim 1, wherein the individual boom arm segments comprise a plurality of component parts affixed together.

11. The medical boom of claim 1, wherein the boom arm segments are made from one of the following types of materials: metal, metal alloy, plastic, or carbon fiber.

12. The medical boom of claim 1, wherein the boom arm joints comprise one of the following types of joints: rotating joints and pin joints.

13. The medical boom of claim 1, wherein the appendage arm segments are rotationally coupled to the associated appendage arm joints.

14. The medical boom of claim 1, wherein the appendage arm segments are rotationally coupled to the associated appendage arm joints in the horizontal plane.

15. The medical boom of claim 1, wherein the appendage arm segments are rotationally coupled to the associated appendage arm joints in the vertical plane.

16. The medical boom of claim 1, wherein the individual appendage arm segments comprise a plurality of component parts affixed together.

17. The medical boom of claim 1, wherein the appendage arm segments are made from one of the following types of materials: metal, metal alloy, plastic, or carbon fiber.

18. The medical boom of claim 1, wherein the appendage arm joints comprise one of the following types of joints: rotating joints and pin joints.

19. The medical boom of claim 1, further comprising a mounting plate coupled to at least one of the plurality of appendage arms, the equipment used in the operating room being configured to be mounted onto the mounting plate.

20. The medical boom of claim 1, wherein at least one boom arm of the plurality of boom arms further comprises a conduit for routing one or more of the following through the at least one boom arm: electrical signal wires, electrical power wires, gas hoses and fluid hoses.

21. The medical boom of claim 1, wherein at least one of the plurality of appendage arms further comprises a conduit for routing one or more of the following through the first articulated arm: electrical signal wires, electrical power wires, gas hoses and fluid hoses.

22. The medical boom of claim 1, further comprising at least one base joint to mount at least one boom arm of the plurality of boom arms onto the stationary base, the at least one base joint enabling the at least one boom arm to be moved in the vertical plane.

23. The medical boom of claim 1, further comprising a connection joint to mount one of the plurality of appendage arms onto one of the plurality of boom arms, the connection joint enabling the one of the plurality of appendage arms to be moved in the vertical plane.

24. A medical boom, comprising:
a stationary base configured to be installed in an operating room;
a boom arm having a first boom arm end and a second boom arm end, the first boom arm end attached to and supported by the stationary base, the boom arm having at least an associated pair of boom arm segments that are coupled together with a boom arm joint;
a first mounting element coupled to a first one of the boom arm segments for supporting a first flat panel video display monitor capable of displaying video images, such that the first flat panel video display monitor may be positioned in three degrees of freedom around the operating field in the operating room by manipulating the position of the boom arm and the first mounting element;
a second mounting element coupled to a second one of the boom arm segments for supporting a second flat panel video display monitor capable of displaying video images, such that the second flat panel video display monitor may be positioned in three degrees of freedom around the operating field in the operating room by manipulating the position of the boom arm and the second mounting element.

25. The medical boom of claim 24, wherein the boom arm further comprises a plurality of joints that enable the boom arm segments to be positioned with respect to one another.

26. The medical boom of claim 24, wherein the boom arm is capable of being positioned in the horizontal direction within the operating field in the operating room.

27. The medical boom of claim 24, wherein the boom arm is capable of being positioned in the vertical direction within the operating field in the operating room.

28. The medical boom of claim 24, wherein the first mounting element is an appendage coupled to the boom arm, the first flat panel video display monitor being mounted onto the appendage arm.

29. The medical boom of claim 28, wherein the appendage arm is an articulated arm comprising a plurality of segments mechanically held together by joints.

30. The medical boom of claim 29, wherein the appendage arm is configured to be positioned in the horizontal and vertical directions.

31. The medical boom of claim 24, wherein the first mounting element is further configured to mount one of the following types of equipment onto the boom arm: a video camera, or audio equipment.

32. The medical boom of claim 24, wherein the boom arm is further configured to provide gases to the operating field.

33. The medical boom of claim 24, wherein the boom arm further comprises a conduit configured to supply and/or recover fluids from the operating field.

34. The medical boom of claim 24, wherein the stationary base is further configured to house electronic equipment for providing medical, video and data processing services for the operating field.

35. The apparatus of claim 24, wherein the first flat panel video display monitor comprises a touch screen monitor configured to allow medical personal in the operating room to control electrical and medical equipment housed in the stationary base.

36. The apparatus of claim 24, wherein the boom arm further comprises a conduit for routing one or more of the following: electrical wires, electrical power wires, gas hoses; and fluid hoses.

37. The apparatus of claim 1, wherein the stationary base is further configured to support up to four of the boom arms.

38. A medical boom, comprising:
a stationary base configured to be installed into an operating room;
a plurality of boom arms, each of the plurality of boom arms being supported by the stationary base and configured to extend over an operating table in the operating room and having at least an associated pair of boom arm segments that are coupled together by a boom arm joint; and
a plurality of appendage arms, each appendage arm being mounted on an associated boom arm and having at least an associated pair of appendage arm segments that are coupled together by an appendage arm joint, each of the appendage arms being configured to support an associated display monitor that can be positioned in the horizontal and the vertical planes substantially surrounding the operating table, wherein the stationary base is further configured to support up to four of the boom arms and wherein the up to four boom arms each attach to a top corner of the stationary base respectively.

39. The apparatus of claim 1, wherein the stationary base is a standing structure having a front panel and a rear panel and two side panels.

40. The apparatus of claim 39, wherein the front panel and the rear panel have one or more recesses to house medical and/or electronic equipment.

41. The apparatus of claim 40, wherein the medical and/or electronic equipment is accessible through either the front panel or the rear panel.

42. The apparatus of claim 39, further comprising one or more shelves attached to either of the two side panels.

43. The apparatus of claim 24, further comprising more than two of the boom arms.

44. The apparatus of claim 24, wherein the stationary base is further configured to support up to four of the boom arms.

45. The apparatus of claim 44, wherein the up to four boom arms each attach to a top corner of the stationary base respectively.

46. The apparatus of claim 24, wherein the stationary base is a standing structure having a front panel and a rear panel and two side panels.

47. The apparatus of claim 46, wherein the front panel and the rear panel have one or more recesses to house medical and/or electronic equipment.

48. The apparatus of claim 47, wherein the medical and/or electronic equipment is accessible through either the front panel or the rear panel.

49. The apparatus of claim 46, further comprising one or more shelves attached to either of the two side panels.

50. A medical boom, comprising:
a stationary base configured to be installed into an operating room;
a plurality of boom arms, each of the plurality of boom arms being supported by the stationary base and configured to extend over an operating table in the operating room and having at least an associated pair of boom arm segments that are coupled together by a boom arm joint; and
a plurality of appendage arms, each appendage arm being mounted on an associated boom arm and having at least an associated pair of appendage arm segments that are coupled together by an appendage arm joint, each of the appendage arms being configured to support an associated display monitor that can be positioned in the horizontal and the vertical planes substantially surrounding the operating table, wherein a first appendage arm and a second appendage arm of the plurality of appendage arms are mounted off a first boom arm of the plurality of boom arms and wherein a third appendage arm and a fourth appendage arm of the plurality of appendage arms are mounted off a second boom arm of the plurality of boom arms.

51. The medical boom of claim 1 further comprising a plurality of display monitors and wherein each of the plurality of appendage arms carries an associated display monitor of the plurality of display monitors.

52. A medical boom, comprising:
a stationary base configured to be installed into an operating room;
a plurality of boom arms, each of the plurality of boom arms being supported by the stationary base and configured to extend over an operating table in the operating room and having at least an associated pair of boom arm segments that are coupled together by a boom arm joint;
a plurality of appendage arms, each appendage arm being mounted on an associated boom arm and having at least an associated pair of appendage arm segments that are coupled together by an appendage arm joint, each of the appendage arms being configured to support an associated display monitor that can be positioned in the horizontal and the vertical planes substantially surrounding the operating table, wherein a first appendage arm of the plurality of appendage arms is mounted on the boom arm joint of a first boom arm of the plurality of boom arms, the first boom arm having a first end and a second end, the boom arm joint of the first boom arm being situated between the first and second ends of the first boom arm.

53. The medical boom arm of claim 52 wherein the first end of the first boom arm is mounted on the stationary base and a second appendage arm of the plurality of appendage arms is mounted on the second end of the first boom arm.

54. The medical boom of claim 1 wherein the stationary base includes a bottom surface and supports an opposing top surface, the bottom surface being mounted over a base plate suitable for securing to the floor, a top boom arm joint extending at least partially from the top surface and wherein one of the plurality of boom arms is coupled with the top surface of the stationary base via the top boom arm joint.

55. The medical boom of claim 1 wherein the plurality of appendage arms include brackets suitable for supporting the associated display monitors.

56. The medical boom of claim 24 wherein the first mounting element is mounted on a distal end of the first one of the boom arm segments.

57. The medical boom of claim 24 wherein the boom arm segments extend between the first boom arm end and the second boom arm end and couple the first boom arm end with the second boom arm end.

58. The medical boom of claim 24 wherein the first mounting element is mounted on the boom arm joint.

\* \* \* \* \*